United States Patent [19]

Inoue et al.

[11] Patent Number: 4,689,176
[45] Date of Patent: Aug. 25, 1987

[54] NOVEL OPTICALLY ACTIVE COMPOUND AND LIQUID CRYSTAL COMPOSITION CONTAINING SAME

[75] Inventors: Hiromichi Inoue; Shinichi Saito; Kazutoshi Miyazawa; Takashi Inukai; Kanetsugu Terashima, all of Yokohamashi, Japan

[73] Assignee: Chisso Corporation, Tokyo, Japan

[21] Appl. No.: 811,757

[22] Filed: Dec. 20, 1985

[30] Foreign Application Priority Data

Dec. 26, 1984 [JP] Japan .................. 59-277077

[51] Int. Cl.$^4$ ............. C09K 19/12; C09K 19/20; C07C 121/38; C07C 69/76
[52] U.S. Cl. ................. 252/299.65; 252/299.67; 252/299.01; 350/350 S; 560/59; 560/72; 560/73; 558/416
[58] Field of Search .............. 252/299.67, 299.65, 252/299.5; 350/350 S, 350 R; 560/59, 72, 73; 260/465 D; 558/416

[56] References Cited

U.S. PATENT DOCUMENTS

| | | | |
|---|---|---|---|
| 4,017,416 | 4/1977 | Inukai et al. | 350/350 R |
| 4,029,594 | 6/1977 | Gavrilouic et al. | 350/350 R |
| 4,065,489 | 12/1977 | Steinstrasser et al. | 252/299.65 |
| 4,083,797 | 4/1978 | Oh | 252/299.66 |
| 4,112,239 | 9/1978 | Dubois et al. | 350/350 S |
| 4,149,413 | 4/1979 | Gray et al. | 350/350 R |
| 4,195,916 | 4/1980 | Coates | 252/299.65 |
| 4,264,148 | 4/1981 | Gobl-Wunsch et al. | 350/350 S |
| 4,340,498 | 7/1982 | Sugimori | 350/350 S |
| 4,424,371 | 1/1984 | Hsu | 252/299.67 |
| 4,473,487 | 9/1984 | Romer et al. | 350/350 R |
| 4,490,277 | 12/1984 | Grebenkin et al. | 252/299.6 |
| 4,576,732 | 3/1986 | Isogai et al. | 252/299.65 |
| 4,596,667 | 6/1986 | Inukai et al. | 252/299.65 |
| 4,614,609 | 9/1986 | Inoue et al. | 252/299.66 |

FOREIGN PATENT DOCUMENTS

| | | | |
|---|---|---|---|
| 19665 | 12/1980 | European Pat. Off. | 252/299.63 |
| 115693 | 8/1984 | European Pat. Off. | 252/299.65 |
| 51-87181 | 7/1976 | Japan | 252/299.67 |
| 52-87138 | 7/1977 | Japan | 252/299.67 |
| 53-44535 | 4/1978 | Japan | 252/299.65 |
| 53-60385 | 5/1978 | Japan | 252/299.67 |
| 53-76984 | 7/1978 | Japan | 252/299.5 |
| 57-165334 | 10/1982 | Japan | 560/73 |
| 59-95255 | 6/1984 | Japan | 252/299.65 |
| 61-22051 | 1/1986 | Japan | 252/299.66 |

OTHER PUBLICATIONS

Li et al., CA 94:191853, 1981.
Goodby et al., Liq. Cryst. Ord. Fluids, vol. 4, 1984, pp. 1–32.
Gray et al., Mol. Cryst. Liq. Cryst., vol. 37, 1976, pp. 157–188.
Gray et al., Mol. Cryst. Liq. Cryst., vol. 37, 1976, pp. 189–211.

Primary Examiner—Teddy S. Gron
Assistant Examiner—J. E. Thomas
Attorney, Agent, or Firm—Wenderoth, Lind & Ponack

[57] ABSTRACT

A novel optically active compound suitable for use in a display mode utilizing a ferroelectric liquid crystal, and a chiral smectic liquid crystal composition containing the same are provided, which novel optically active compound is expressed by the formula

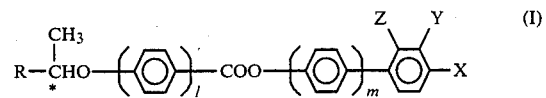

wherein R represents an alkyl group of 2 to 15 carbon atoms; X represents CN group or a halogen atom; Y and Z each represent a halogen atom or hydrogen atom, but either one of Y and Z is hydrogen atom; l is 1 or 2; m is 0 or 1; and a symbol * shows that the carbon atom having this symbol attached thereto constitutes an optically active center.

8 Claims, No Drawings

NOVEL OPTICALLY ACTIVE COMPOUND AND LIQUID CRYSTAL COMPOSITION CONTAINING SAME

BACKGROUND OF THE INVENTION

1. Field of the Invention

This invention relates to a novel optically active compound and a liquid crystal composition containing the same. More particularly it relates to a novel optically active carboxylic acid substituted-phenyl ester and a chiral, smectic liquid crystal composition containing the same.

2. Description of the Prior Art

Among liquid crystal display elements, those of twisted nematic (TN) type display mode have currently been most widely used, but they are inferior in response rate to emissive type display elements (e.g. electroluminescence, plasma display, etc.), and various improvements in this respect have been attempted, but it appears, nevertheless, that the possibility of notable improvement remains. Thus, various liquid crystal display devices based on a different principle from that of TN type display elements have been tried. Among these devices, there is a device of display mode utilizing ferroelectric liquid crystals (N. A. Clark et al, Applied Phys. lett., 36, 899 (1980)). This mode utilizes the chiral smectic C phase (hereinafter abbreviated to SC* phase), the chiral smectic H phase (hereinafter abbreviated to SH* phase) or the like of ferroelectric liquid crystals, and substances having such phases in the vicinity of room temperature have been desired as those suitable to this mode.

Mainly in order to develop liquid crystal substances suitable for use in such a display mode, the present inventors have extensively searched for various liquid crystal compounds and compounds similar thereto each having an optically active group, and as a result have found an optically active compound of the present invention.

SUMMARY OF THE INVENTION

The present invention resides in an optically active compound expressed by the formula

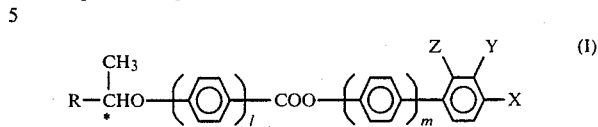

wherein R represents an alkyl group of 2 to 15 carbon atoms; X represents the CN group or a halogen atom; Y and Z each represent a halogen atom or hydrogen atom, but either one of Y and Z is hydrogen atom; l is 1 or 2; m is 0 or 1; and the symbol * shows that the carbon atom having this symbol attached thereto constitutes an optically active center, and a chiral smectic liquid crystal composition containing at least two components at least one of which is said optically active compound.

DESCRIPTION OF PREFERRED EMBODIMENTS

The phase transition points of representative compounds among those of the formula (I) are shown in the following Table 1:

TABLE 1

| Sample No. | In formula (I) | | | | | Phase transition points (°C.) | | | | | Remarks |
|---|---|---|---|---|---|---|---|---|---|---|---|
| | l | m | X | Y | Z | C | | SA | Ch | I | |
| 1 | 1 | 0 | Cl | H | Cl | · | 12.0 | — | — | · | |
| 2 | 1 | 0 | F | Cl | H | | oil | — | — | · | |
| 3 | 1 | 0 | Cl | Cl | H | | oil | — | — | · | |
| 4 | 1 | 0 | CN | F | H | | oil | — | — | · | |
| 5 | 1 | 0 | CN | Cl | H | · | 38.5 | — | — | · | |
| 6 | 1 | 0 | Br | F | H | · | 21.8 | — | — | · | |
| 7 | 1 | 0 | CN | H | H | · | 9.0 | — | — | · | |
| 8 | 1 | 0 | F | H | H | · | 30.0 | — | — | · | |
| 9 | 1 | 1 | Br | H | H | · | 134.5 | · 147.8 | — | · | Example 2 |
| 10 | 2 | 0 | F | F | H | · | 68.0 | · 116.8 | — | · | |
| 11 | 2 | 0 | F | H | F | · | 68.0 | (· 44.9) | (· 50.7) | · | |
| 12 | 2 | 0 | CN | F | H | · | 46.8 | · 92.5 | · 100.0 | · | |
| 13 | 2 | 0 | CN | Cl | H | · | 55.5 | (· 34.1) | (· 41.1) | · | |
| 14 | 2 | 0 | CN | H | F | · | 84.5 | — | · 114.3 | · | |
| 15 | 2 | 0 | Br | H | F | · | 87.0 | (· 82.1) | — | · | |
| 16 | 2 | 0 | F | H | H | · | 108.7 | · 132.0 | — | · | Example 1 |
| 17 | 2 | 0 | Cl | H | H | · | 117.0 | · 161.7 | — | · | |
| 18 | 2 | 0 | Br | H | H | · | 121.8 | · 164.3 | — | · | |
| 19 | 2 | 0 | CN | H | H | · | 84.0 | · 133.0 | · 141.2 | · | |

Note:
1. R in the formula (I) of these samples represents n-$C_6H_{13}$.
2. In the Table, phase symbols C, SA, Ch and I represent crystalline, smectic A, cholesteric and isotropic liquid crystal phases, respectively; symbol · shows that one of the phases is present there and the symbol — shows that it is absent there; the numeral figure on the right side of a symbol · (a phase) exhibits the phase transition point from the symbol · (the phase) to the right adjacent symbol ·.

In the case of most of the compounds of the formula (I) wherein l=1 and m=0, no liquid crystal phase is observed, whereas mainly in the case of the compounds of the formula (I) wherein l=1 and m=1 or wherein l=2 and m=0, a liquid crystal phase is observed. Further, even in the case where a liquid crystal phase is exhibited, the liquid crystal phase is smectic A phase or cholesteric phase. In view of this fact, the compounds of the present invention are liable to be regarded as unsuitable as a component of the above ferroelectric liquid crystal composition. However, it will be appreciated from the following description that the above judgement is unjustified.

The compounds of formula (I) of the present invention are unsuitable for use as a ferroelectric liquid crystal by themselves, but is has been found that by adding the compound to a material having another phase, i.e., chiral smectic C phase (SC* phase) or smectic C phase (SC phase), it is possible to obtain a liquid crystal material having an extremely large value of spontaneous polarization (Ps). The Ps value of the compounds of the formula (I) as estimated by the extrapolation method amounts to about 80 nC/cm$^2$. Since this value is not the one obtained by observing the compound of the formula (I) itself, it cannot be regarded namely as the Ps value of the compound of the formula (I), but the fact that the compound has such a function and effectiveness in practical use is extremely useful and surprising.

On the other hand, for example a compound disclosed in Japanese patent application laid-open No. Sho 53-22883/1978 and having the general formula

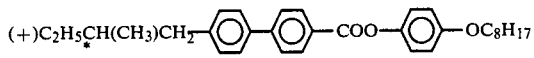

has a Ps value of about 1 nC/cm$^2$ when measured by the present inventors. Thus, it can be said that the compound of the present invention has an extremely great effectiveness of enhancing Ps value.

In addition, even known ferroelectric liquid crystal compounds other than the above have a Ps value of at most about 20.

Display elements exhibiting the light-switching effect of SC* phase have the following three superior specific features as compared with those of TN display mode:

The first specific feature is that the display elements reply at a very high rate so that the response time is 1/100 or less of those of conventional TN mode display elements. The second specific feature is that there is a memory effect so that the multiplex drive is easy in combination thereof with the above high rate response properties. The third specific feature is that when the gray scale is given in the case of TN display mode, this is effected by adjusting the impressed voltage, but there are raised difficult problems such as temperature dependency of threshold voltage, temperature dependency of response rate, etc.; whereas when the light-switching effect of SC* phase is applied, it is possible to readily obtain the gray scale by adjusting the reverse time of polarity and hence the display elements are very suitable to graphic display.

As to the display method, the following two may be considered:

One method is of birefringence type using two plates of polarizers and another is of guest-host type using a dichlroic dyestuff. Since SC* phase has a spontaneous polarization, the molecule is reversed around the helical axis as a rotating axis by reversing the polarity of impressed voltage. When a liquid crystal composition having SC* phase is filled in a liquid crystal display cell subjected to aligning treatment so that the liquid crystal molecules can be aligned in parallel to the electrode surface, followed by placing the liquid crystal cell between two plates of polarizers arranged so that the director of the liquid crystal molecules can be in parallel to the polarization plane on one side, impressing a voltage and reversing the polarity, then a bright field of view and a dark field of view are obtained depending on the opposition angle of the polarizers. On the other hand, in the case of operation by way of the guest-host type, it is possible to obtain a bright field of view and a colored field of view (depending on the arrangement of the polarization plate), by reversing the polarity of impressed voltage.

In general, it is difficult to align liquid crystal molecules in parallel to the wall surface of glass plate in the smectic state thereof; hence liquid crystal molecules have been aligned by very slowly cooling the molecules starting from the isotropic liquid thereof (1° C.~2° C./hr) in a magnetic field of several tens gausses or more. But, in the case of a liquid crystal substance exhibiting the cholesteric phase thereof in a temperature range higher than the temperature at which the smectic phase is exhibited, it is possible to easily obtain a uniformly aligned monodomain state, by cooling the molecules from the temperature at which the cholesteric phase thereof is exhibited, down to the temperature at which the smectic phase is exhibited, at a cooling rate of 1° C/min., while impressing a direct current voltage of 50 to 100 V in place of the magnetic field.

The compound of the formula (I) of the present invention is suitable as a component of SC* compositions used in the display mode utilizing the chiral, smectic liquid crystal phase, as shown in the foregoing and in the Examples described below, but, in this case, it can be said that compounds which exhibit the liquid crystal phase by themselves are generally preferable to those which do not exhibit it.

Still another surprising specific feature of the compounds of the formula (I) will be described below. Since the compounds of the formula (I) of the present invention are optically active substances, their addition to a nematic liquid crystal naturally affords a chiral nematic phase (cholesteric phase), that is, induces a twisted structure, but at that time, an abnormal behavior is observed that the cholesteric pitch (P) induced by a compound of the formula (I) is shifted to a longer one due to temperature reduction.

For example, when compounds of the formula (I) are added each in 4% by weight to ZL1-1132 (tradename of a nematic liquid crystal of a 4(4'-alkylcyclohexyl)-benzonitrile made by Merck Company), the respective cholesteric pitches of the resulting chiral, nematic (cholesteric) liquid crystals become longer with temperature reduction, as shown in Table 2.

TABLE 2

| Additive | Temperature change of cholesteric pitch (P) | | |
|---|---|---|---|
| | P (in μm) at | | |
| | 20° C. | 30° C. | 40° C. |
| Sample No. 7 | 18.2 | 15.0 | 13.1 |
| Sample No. 5 | 25.9 | 21.6 | 18.8 |
| Sample No. 6 | 29.7 | 23.3 | 20.4 |

The above-mentioned behavior is contrary to the temperature change of the cholesteric pitch induced by generally known optically active substances.

The practical importance of the compounds of the formula (I) based on the above surprising specific feature of the compound is evident from the detailed description of other Japanese patent applications No. Sho. 60-170,951/1985 and No. Sho 60-172,090/1985 both filed by Emoto et al who are our research colleagues. Thus, although the details are not described herein, a part thereof will be summarized as follows:

As described above, when the optically active substance of the present invention is added to a nematic liquid crystal, the cholesteric pitch of the resulting liquid crystal composition, induced thereby becomes longer with temperature reduction, contrary to the usual case; hence a superior effectiveness is observed that there is reduced the temperature dependence of the threshold voltage in the electro-optic effect of twisted nematic displays using the liquid crystal composition, whereas in the usual case, generally the threshold voltage increases unfavorably with temperature reduction.

According to a known method of reducing the temperature dependence of the threshold voltage, an optically active substance which induces a right-twisted cholesteric helical structure and an optically active substance which induces a left-twisted cholesteric helical structure are both added to thereby reduce the residual twisting power due to temperature reduction, based on the difference between the temperature dependences of the respective twisting powers (that is, the cholesteric pitch increases with the temperature reduction) (e.g. see Japanese patent application laid-open No. Sho. 55-38869/1980). In comparison with this known method, the above-mentioned novel method is far superior.

Further, since the compound of the formula (I) contains an optically active carbon atom, it has a capability of inducing a twisted structure when added to a nematic liquid crystal. A nematic liquid crystal having a twisted structure, i.e., a chiral nematic liquid crystal, does not form the so-called reverse domain of TN type display elements; hence it is possible to use the compound of the formula (I) as an agent for preventing the reverse domain from forming. Preparation of the compound of the formula (I)

The compounds of the formula (I) can be prepared via the following course:

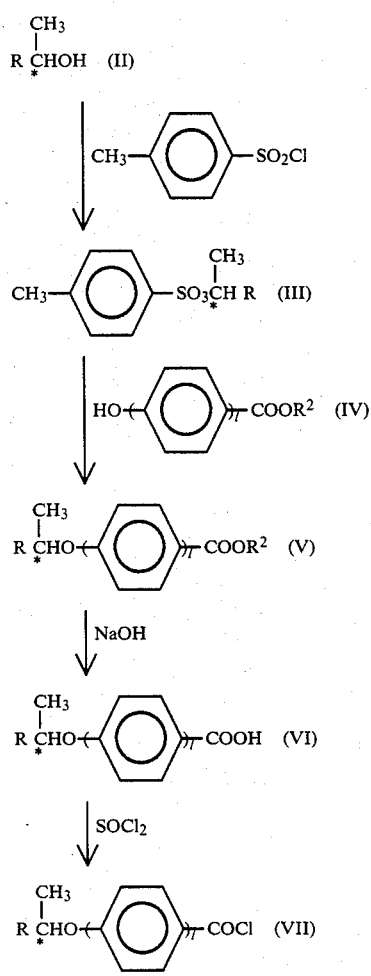

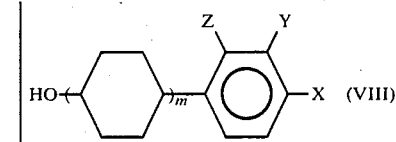

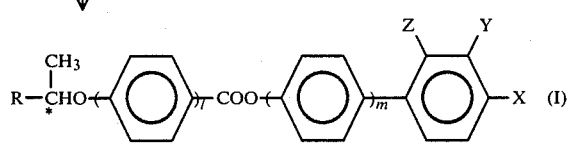

In the above scheme, $R^2$ represents a short chain alkyl group and other symbols are as defined above.

In the above scheme, first an optically active 1-methyl-1-alkanol (II) which is a known compound is reacted with p-toluenesulfonic acid chloride in the presence of pyridine to obtain a compound (III) which is then reacted with a compound (IV) (a p-hydroxybenzoic acid alkyl ester or a 4-hydroxy-4'-biphenylcarboxylic acid alkyl ester) in the presence of KOH to obtain a compound (V) which is then hydrolyzed in the presence of aqueous NaOH to obtain a compound (IV) which is then reacted with thionyl chloride to obtain a compound (VII) which is reacted in the presence of pyridine with a phenol (VIII) corresponding to a final objective compound, such as p-cyanophenol, p-fluorophenol, p-chlorophenol, p-bromophenol, p'-hydroxy-p-cyanobiphenyl, p'-hydroxy-p'-fluorobiphenyl, p'-hydroxy-p-chlorobiphenyl, p'-hydroxy-p-bromophenyl, 2,4-difluorophenol, 3,4-difluorophenol, 2-fluoro-4-cyanophenol, 3-fluoro-4-cyanophenol, 2-fluoro-4-bromophenol, 3-fluoro-4-bromophenol, 3-chloro-4-cyanophenol, 3-chloro-4-fluorophenol, etc. to obtain the objective compound of the formula (I).

In addition, among the raw material optically active 2-alkanols, S(+)-2-octanol and R(−)-2-octanol are readily commercially available, but other optically active 2-alkanols are at present unsuitable for use in a large quantity. The present inventors used as raw material, products obtained by subjecting racemic substances to optical resolution according to the description of a literature (R. H. Pickard et al. J. Chem. Soc., 99, 45 (1911)), and by using the thus obtained optically active 2-alkanols, it is possible to obtain various compounds of the formula (I) having different kinds of R. However, change in the liquid crystal phase transition points depending on the chain length of R is slight; hence it has no particular advantage to use as raw material, optically active 2-alkanols other than 2-octanol which is most readily commercially available.

The optically active ester compounds of the present invention will be described in more detail by way of Examples.

The following Examples disclose only those wherein S(+) type compounds are used as the raw material optically active 2-alkanol, but even when R(−) type 2-alkanols are used as raw material, the objective compounds having the same phase transition points as in the case of S(+) type compounds are obtained. This is natural from the theoretical viewpoint. However, the angle of rotation, twist direction of helix and direction of spontaneous polarization in the case of R(−) type compounds are contrary to those in the case of S(+) type compounds.

As to the objective compounds obtained from S(+)-2-alkanols as raw material, the twist direction of helix of the induced cholesteric phase is left direction and the direction of spontaneous polarization is (+).

EXAMPLE 1

Preparation of optically active 4'-(1-methylheptyloxy)-4-biphenylcarboxylic acid p-fluorophenyl ester (a compound of the formula (I) wherein l=2, m=0, R=$C_6H_{13}$, X=F and Y, Z=H; sample No. 16) S(+)-2-octanol (200 g, 1,536 mol) was dissolved in dry pridine (06600 ml and to the resulting solution was dropwise added a solution obtained by dissolving p-toluenesulfonic acid chloride (292.8 g, 1.536 mol) in dry tolune (440 ml) while keeping the temperature inside the system lest it exceed 10° C., followed by stirring the mixture at room temperature for one hour, raising the temperature inside the system to 50° C., keeping this temperature for 2 hours, then cooling, further adding water (1 l) and toluene (500 ml), stirring the mixture, washing the separated toluene layer with 6N—HCl, then with 2N—NaOH aqueous solution and further with water till the washing water became neutral, and distilling off toluene to obtain as a residue, optically active p-toluenesulfonic acid 1-methyl-heptyl ester (III) (321.0 g).

On the other hand, 4-hydroxy-4'-biphenylcarboxylic acid ethyl ester (IV) (38.7 g, 0.160 mol) was dissolved in ethanol (200 ml), and KOH (9 g, 0.160 mol) was added to and dissolved in the solution, followed by adding optically active toluenesulfonic acid 1-methyl-heptyl ester (50 g, 0.176 mol) obtained above, keeping the mixture under reflux for 4 hours, then cooling, adding toluene (200 ml) and 6N—HCl (50 ml), washing the resulting toluene layer with 2N—NaOH aqueous solution and further with water till the washing water became neutral, and distilling off toluene to obtain as a residue, optically active 4'-(1-methyl-heptyloxy)-4-biphenylcarboxylic acid ethyl ester (V) (38.6 g). This product (38.6 g, 0.109 mol) was dissolved in ethanol (6 ml), NaOH (5.3 g, 0.130 mol) and water (26 ml), followed by heating the solution under reflux for 10 minutes to deposit crystals, cooling, adding 6N—HCl (20 ml) to filter off crystals and further recrystallizing from acetic acid to obtain optically active 4'-(1-methyl-heptyloxy)-4-biphenylcarboxylic acid (VI) (23.4 g). This product exhibited liquid crystal phases and the phase transition points were as follows: C-SC* point 160° C., SC*-Ch point 177° C. and Ch-I point 196° C.

To this product (20 g, 0.063 mol) was added thionyl chloride (11.3 g, 0.095 mol), followed by heating the mixture under reflux for one hour, and distilling off excess thionyl chloride to obtain optically active 4'-(1-methyl-heptyloxy)-4-biphenylcarboxylic acid chloride (VII) (21 g).

This product (2.0 g, 0.006 mol) was added to and reacted with a solution of p-fluorophenol (VIII) (0.78 g, 0.007 mol) dissolved in pyridine (5 ml), followed by heating the reaction mixture with stirring, allowing to stand overnight, then adding toluene (30 ml) and water (20 ml), stirring, washing the resulting toluene layer with 6N—HCl, then with 2N—NaOH aqueous solution and further with water till the washing water became neutral, distilling off toluene and recrystallizing the residue from ethanol to obtain the objective optically active 4'-(1-methyl-heptyloxy)-4-biphenylcarboxylic acid p-fluorophenyl ester (1.3 g). Its phase transition points were as follows: C-SA point 108.7° C. and SA-I point 132.0° C.

The absolute steric configuration of this substance could not yet have been determined, but since it is considered that Walden inversion occurred at the stage of preparing the compound (V), the absolute steric configuration is presumed to be of R. Further, the values of elemental analysis of the substance accorded well with the calculated values as follows:

|   | Observed value | Calculated value (in terms of $C_{27}H_{29}O_3F_1$) |
|---|---|---|
| C | 77.00% | 77.12% |
| H | 6.30% | 6.95% |
| F | 4.40% | 4.52% |

EXAMPLE 2

Preparation of optically active p-(1-methylheptyloxy)benzoic acid 4'-bromo-4-biphenylyl ester (a compound of the formula (I) wherein l=1, m=1, R=$C_6H_{13}$, X=Br and Y, Z=H; Sample No. 9) P-hydroxybenzoic acid methyl ester (IV) (28.5 g, 0.187 mol) was dissolved in methanol (120 ml), and KOH (10.1 g, 0.187 mol) was added to and dissolved in the solution, followed by adding to the resulting solution, optically active p-toluenesulfonic acid 1-methyl-heptyl ester (III) (58.6 g, 0.206 mol) obtained in Example 1, keeping the mixture under reflux for 4 hours, then cooling, adding toluene (200 ml) and 6N—HCl (50 ml), washing the resulting toluene layer with 2N—NaOH aqueous solution and then with water till the washing water became neutral and distilling off toluene to obtain as a residue, optically active p-(1-methyl-heptyloxy)-benzoic acid methyl ester (V) (14.2 g). This ester (14.2 g, 0.054 mol) was dissolved together with ethanol (5 ml), NaOH (3.2 g, 0.081 mol) and water (20 ml), followed by heating the solution under reflux for one hour, then cooling, pouring the reaction fluid in 6N—HCl aqueous solution (50 ml) with stirring, filtering off deposited crysrals and recrystallizing from ethanol to obtain optically active p-(1-methyl-butyloxy)benzoic acid (VI) (8.1 g) having a melting point of 61.2°~63.1° C. To this product (7.5 g, 0.030 mol) was added thionyl chloride (6.0 g, 0.047 mol), followed by heating the mixture under reflux for one hour, and distilling off excess thionyl chloride to obtain opticaly active p-(1-methyl-heptyloxy)benzoic acid chloride (VII) (5.8 g).

This product (VII) (1.1 g, 0.004 mol) was added to and reacted with a solution obtained by dissolving 4-(4'-bromophenyl)phenol (VIII) (1.0 g, 0.004 mol), followed by heating the mixture with stirring, then allowing to stand overnight, adding toluene (30 ml) and water (20 ml), stirring the mixture, washing the resulting toluene layer with 6N—HCl, then with 2N—NaOH aqueous solution and further with water till the washing water became neutral, distilling off toluene and recrystallizing from ethyl acetate to obtain the objective optically active p-(1-methyl-heptyloxy)-4-bromo-4-biphenylyl ester (I) (0.8 g). Its phase transition points were as follows: C-SA point 134.5° C., and SA-I point 147.8° C.

Further, the values of elemental analysis of this product accorded well with the calculated values.

|   | Observed value | Calculated value (in terms of $C_{27}H_{29}O_3F_1$) |
|---|---|---|
| C | 79.80% | 77.12% |
| H | 6.50% | 6.95% |

-continued

| | Observed value | Calculated value (in terms of $C_{27}H_{29}O_3F_1$) |
|---|---|---|
| F | 4.32% | 4.52% |

EXAMPLE 3 (Use example 1)

A nematic liquid crystal composition consisting of

| | |
|---|---|
| 4-ethyl-4'-cyanobiphenyl | 20% by weight, |
| 4-pentyl-4'-cyanobiphenyl | 40% by weight, |
| 4-octyloxy-4'-cyanobiphenyl | 25% by weight, and |
| 4-pentyl-4'-cyanoterphenyl | 15% by weight | was filled in a cell composed of two opposed substrates each having a transparent electrode coated with polyvinyl alcohol (PVA) as an aligning agent, followed by rubbing the resulting surface to subject it to a parallel aligning treatment, and having a distance between the electrodes of 10 μm, to prepare a TN type display cell, which was then observed under a polarization microscope. As a result it was observed that a reverse twist domain was formed.

To the above nematic liquid crystal composition was added a compound of the formula (I) of the present invention wherein l=2, m=0, X=CN, Y, Z=H and R=$C_6H_{13}$ (sample No. 19) in a quantity of 0.1% by weight, and the resulting composition was filled in the same cell as above to prepare a TN type display cell, which was then observed as above. As a result the above reverse twist domain was dissolved and a uniform nematic phase was observed.

EXAMPLE 4 (Use example 2)

A chiral, smectic liquid crystal composition containing a compound of the present invention, 4'-(1-methylheptyloxy)-4-biphenylcarboxylic acid p-fluorophenyl ester (sample No. 16 in Table 1) as a component and having the following composition was prepared:

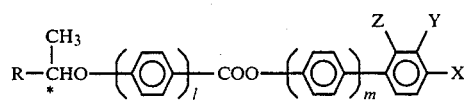

10% by weight (Compound of Sample No. 16)

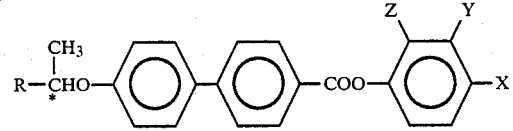

The above composition was prepared by weighing the above 4 kinds of liquid crystal compounds in definite quantities by weight, respectively and dissolving and mixing together these compounds on heating in a sample bottle.

Using the resulting chiral, smectic liquid crystal composition, a liquid crystal element for experiment was prepared. Namely, two glass substrates each provided with a transparent electrode of indium oxide was coated with PVA, followed by rubbing the surface of the resulting film in a definite direction and placing glass fibers of 4 μm in diameter as a spacer therebetween so that the rubbing direction of the two substrates might be parallel, to compose a liquid crystal cell in which the above liquid crystal composition was then sealed in vacuo. The resulting liquid crystal element was placed between two crossed polarizers and an electric field was impressed thereto. As a result, change in the intensity of transmitted light through impression of 20 V was observed.

Response time was calculated from the change in the intensity of transmitted light at that time to exhibit a value of about 1.3 m.sec at 25° C.

In addition, as to the above liquid crystal composition, the temperature change in the texture was observed by means of a polarization microscope. As a result, it was found that the composition turned to a ferroelectric liquid crystal in the temperature range of 20° to 45° C., and the value of its spontaneous polarization was 12 nC/cm$^2$ at 25° C.

On the other hand, a liquid crystal composition excluding the compound of Sample No. 16 of the present invention from the above liquid crystal composition has a value of spontaneous polarization of 3 nC/cm$^2$ at 25° C. Thus it has been confirmed that use of the compound of the present invention greatly increases the value of spontaneous polarization of the chiral smectic liquid crystal composition.

What we claim is:

1. An optically active compound of the formula $$\begin{array}{c} CH_3 \\ | \\ R-CHO \\ * \end{array} -\!\!\left(\!\!\bigcirc\!\!\right)_l\!\!- COO -\!\!\left(\!\!\bigcirc\!\!\right)_m\!\!-\!\!\bigcirc\!\!\begin{array}{c} Z \quad Y \\ \\ \end{array}\!\!-X$$

wherein R represents an alkyl group of 2 to 15 carbon atoms, X represents CN or a halogen atom, Y and Z each represents a halogen atom or hydrogen but at least one of Y and Z is hydrogen, l is 1 or 2, m is 0 or 1 but l+m is 1 or 2 and the symbol * shows that the carbon atom having this symbol attached thereto constitutes an optically active center.

2. An optically active compound according to claim 1, wherein l is 1 and m is 0.

3. An optically active compound according to claim 1, wherein l is 1 and m is 1.

4. An optically active compound according to claim 1, wherein R represents n—$C_6H_{13}$.

5. An optically active compound of the formula $$\begin{array}{c} CH_3 \\ | \\ R-CHO \\ * \end{array} -\!\!\bigcirc\!\!-\!\!\bigcirc\!\!- COO -\!\!\bigcirc\!\!\begin{array}{c} Z \quad Y \\ \\ \end{array}\!\!-X$$

wherein R represents an alkyl group of 2 to 15 carbon atoms, X represents CN or a halogen atom, Y and Z each represents a halogen atom or hydrogen but at least one of Y and Z is hydrogen, and the symbol * shows that the carbon atom having this symbol attached thereto constitutes an optically active center.

6. An optically active compound according to claim 5 wherein X represents CN and one of Y and Z is hydrogen and the other is F.

7. A chiral smectic liquid crystal composition having at least two components at least one of which is an optically active compound of the formula set forth in claim 1.

8. A chiral smectic liquid crystal composition having at least two components at least one of which is an optically active compound of the formula set forth in claim 5.

* * * * *